United States Patent [19]
Milorad

[11] Patent Number: 4,702,739
[45] Date of Patent: Oct. 27, 1987

[54] HOLDER FOR A SYRINGE TO FACILITATE INJECTION PROCEDURE

[76] Inventor: Milosevic M. Milorad, Dimitrija Tucovica 45, 11000 Beograd, Yugoslavia

[21] Appl. No.: 903,778

[22] Filed: Sep. 4, 1986

[30] Foreign Application Priority Data

Nov. 27, 1985 [YU] Yugoslavia ............................ 1847/85
Jan. 20, 1986 [YU] Yugoslavia ............................ 1374/86

[51] Int. Cl.$^4$ .............................................. A61M 5/32
[52] U.S. Cl. ..................................... 604/198; 604/263
[58] Field of Search ............... 604/198, 197, 192, 136, 604/263, 158

[56] References Cited

U.S. PATENT DOCUMENTS 3,073,306  1/1963  Linder ................................. 604/198

FOREIGN PATENT DOCUMENTS 1076898  3/1960  Fed. Rep. of Germany ...... 604/136
1080887  12/1954  France ................................ 604/136

Primary Examiner—John D. Yasko
Attorney, Agent, or Firm—Hoffmann, Dilworth, Barrese & Baron

[57] ABSTRACT

A device for holding a hypodermic syringe-needle unit is provided with a bore in which the syringe unit is received with the needle extending both the holder. A sleeve extended from the holder protectively covers the needle so that the sleeve can be placed against the body part where injection is to occur and with the needle tip end proximate the body part. By sliding the holder toward the body part a detent restraint holding the sleeve in extended position is overcome and relative retraction movement effected therewith and needle insertion smoothly produced to a defined depth without causing any noticeable discomfort to the user.

12 Claims, 8 Drawing Figures

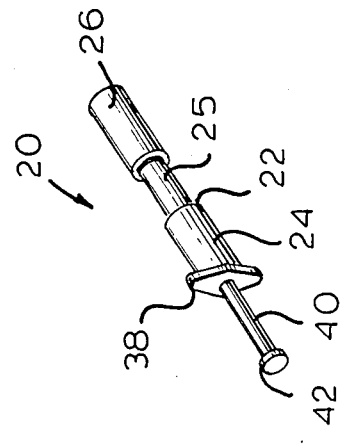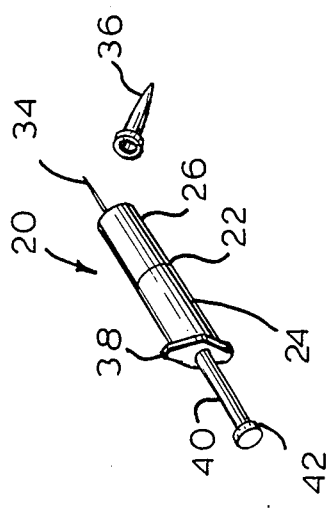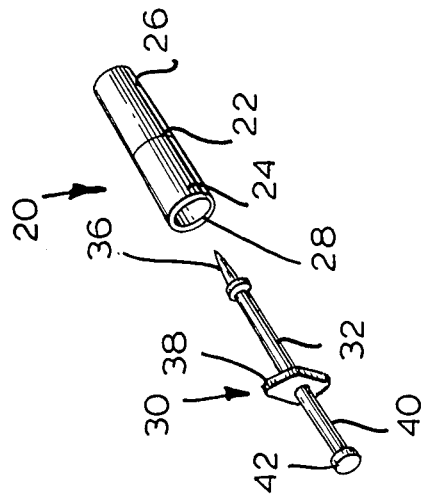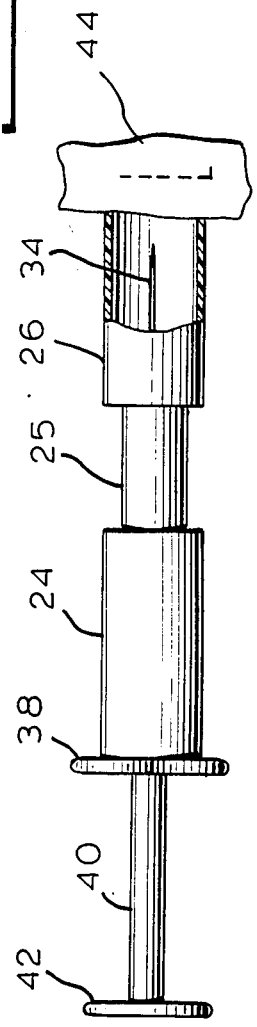

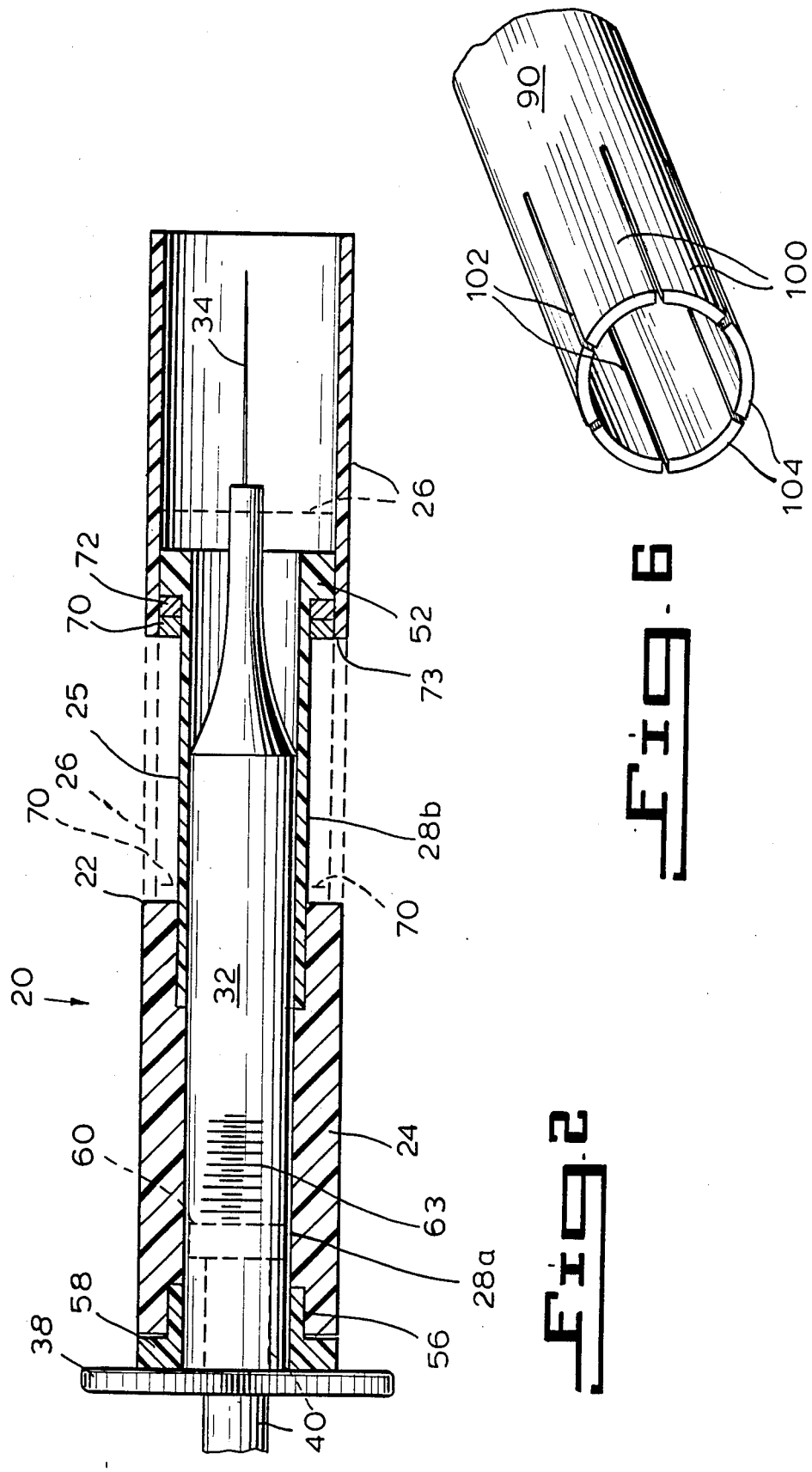

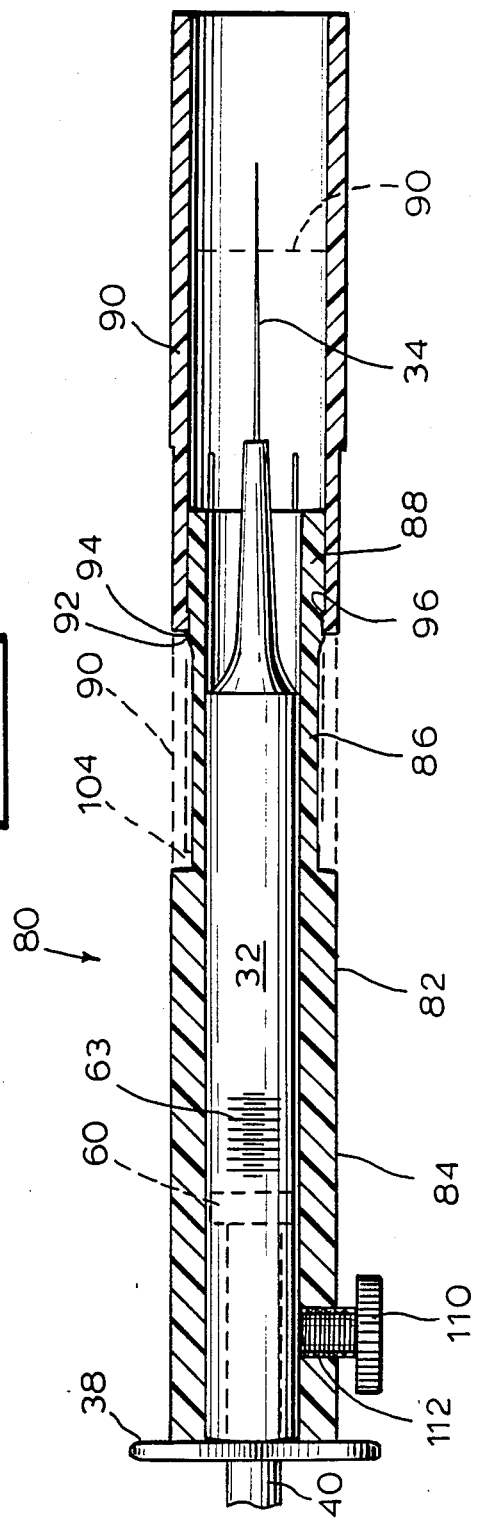
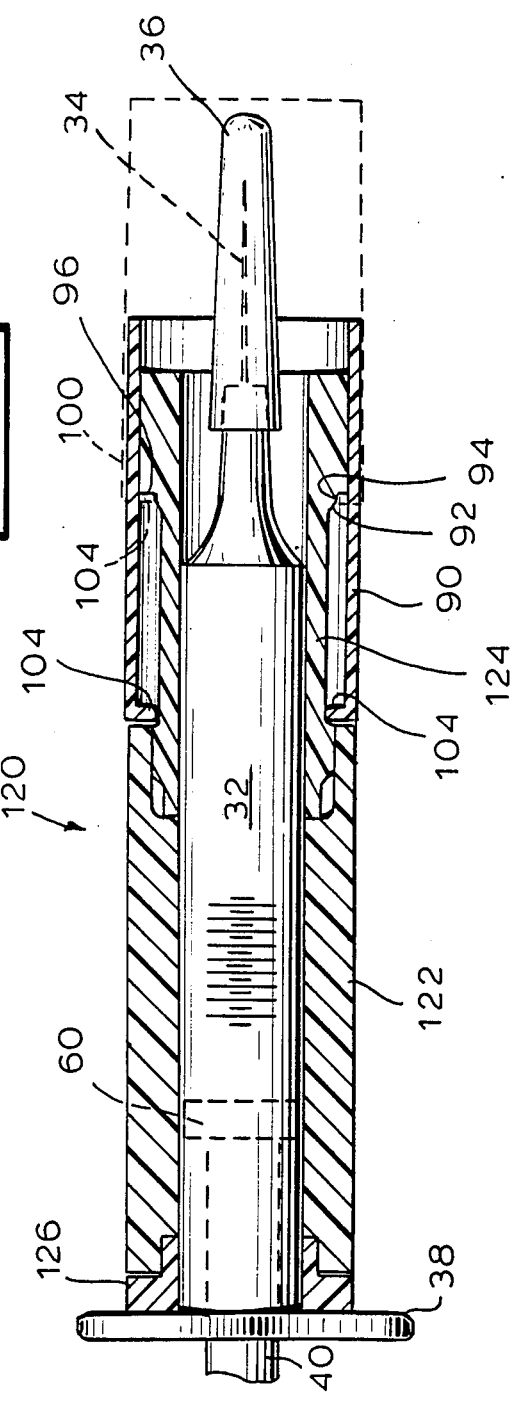

HOLDER FOR A SYRINGE TO FACILITATE INJECTION PROCEDURE

BACKGROUND OF THE INVENTION

This invention relates to a medical device and more particularly to a holder in which a syringe-needle unit can be held to facilitate the needle insertion procedure as an adjunct of administering medication from the syringe or alternatively in aspirating body fluid samples for test purposes.

The prospect of receiving, or as for example, in the instance of insulin-dependent diabetics, the self-administering of an injection can cause anxiety or even trepidation in the mind of the recipient and this can be particularly true in the case of children. While many medical nurses, technicians and the like become adept at administering injections, there are nonetheless occasions when the insertion of the needle into a recipient's body is accompanied by unnecessary pain and discomfort as where an unintentional movement or pressure may be exerted by the technician. This also can be manifest where the injection is totally under the control of the recipient where self-administering of medication such as insulin is practiced. To overcome some of the disadvantages associated with injection procedures and in an effort to standardize or provide constant repeatability of the needle injection movement, injectors or holders for the syringe-needle unit were developed. While these known types of injectors have helped to some extent especially for use where self-administered injection is involved, they still present a number of problems in use. For one thing all these injectors utilize spring mechanisms to control needle insertion movement. However the release of the spring produces vibratory or shaking motion in the needle that detracts from the safety of the insertion and can be the cause of considerable discomfort or even pain for the user. Thus one of the principal aims in having provided an injector is thwarted because the construction and use of same is supposed to reduce the pain effect of an injection.

Further, these types of injectors generally require sterilization of the components thereof prior to use. Because it is difficult to assume that the user is always in a position to provide the conditions required for sterilization, this requirement can be a detriment to successful use of such injectors. In addition, some of the injectors require assembly of components about the syringe-needle unit and if same are not sterile the needle can become contaminated by contact thereof with a component, a not uncommon happening.

The majority of known injectors do not give proper attention to injector size and shape, aspects which are very consequential for proper and effective use of such devices. From the standpoint of technical simplicity and inexpensive costs, known injectors are almost all lacking in measuring up to these criteria. These known devices are for the most part complicated in construction and relatively expensive and so to the point that they are produced only in small quantities.

Accordingly, it is desirable that a relatively simple, sure operating and economically produced type of such device be provided especially in terms of its suitability for use by persons, mainly diabetics, who must self-administer medication by injection method.

SUMMARY OF THE PRESENT INVENTION

An object of the present invention is to provide a device for facilitating insertion of a hypodermic needle into the human body so that the injection procedure is effected with minimum pain and discomfort to the person.

Another object is to provide a device that operates to control injection with constancy and repeatability in that substantially the same insertion force can be applied during the repeated use of the device thereby establishing in the mind of the constant user such as a diabetic, an awareness and acceptance of more minimized discomfort as may attend same and especially as compared to the discomfort associated with injection without use of a device or with prior art devices.

A further object is to provide such a device that is of simplified construction, easy and sure to operate, inexpensively manufactured and thus more readily available to users and which is particularly beneficial to use in connection with administering medication to children.

In accordance with the invention, the device comprises an elongated holder provided with a through bore in which a hypodermic syringe-needle unit can be inserted, the syringe previously having been loaded in the usual manner with the medicament to be administered, and the syringe being friction fit or otherwise held securely within the holder and in such manner that the needle thereof extends beyond one end of the holder. A sleeve is captively received on the holder and is slidable thereon from a retracted position wherein one end thereof is generally proximate the one end of the holder to a second extended position wherein the sleeve encircles the needle and its said one end projects beyond the needle tip end. Cooperating detent means are carried on the sleeve and the holder and operate when the sleeve has been slid to extended position to hold it there in manner as inhibits accidental or placement positioning of the injector against the body part initiation of retraction sliding of the sleeve. This held positioning of the sleeve thus is provided to allow the user to contactingly place and align the one end of the sleeve against the body part for positioning the needle tip end proximate said body part as a necessary preliminary to making the injection. The detent means is, however, of character such as to be readily releasable under the impetus of the force resulting from the user effecting unitary needle insertion movement of the holder and syringe-needle unit in the direction of the body part. The needle insertion movement force need only be that sufficient to overcome the detent resistance and this is not of such magnitude as to require insertion force that gives rise to discomfort. The force required has been observed to allow for smooth, quick and consistent needle insertion unaccompanied by any noticeably disagreeable pain or adverse patient reaction. The unitary movement of the holder and syringe is terminated by abutment of the holder against the sleeve end remote from the body part and this correspondingly limits the depth of needle penetration which would of course be the same depth for each use by reason of the constant sleeve length.

The detent means can be provided in various forms, being in one embodiment a laterally widened part on the holder body and resiliently yieldable structure on the sleeve which yields to engage the laterally widened part but by yielding thereby applying holding bias to maintain the sleeve detented. A particularly advantageous form of detent means involves use of magnets or a magnet and/or ferromagnetic material on the holder and the sleeve, the magnets being magnetically attracted one with the other to effect the sleeve detenting. Magnets are especially satisfactory in that the release force required to separate same is of constant value.

The invention also provides that the holder can be made as a single-piece component having two integral sections of different diameter, or it could be made of two aligned removably connected members, one being of smaller diameter than the other and the sleeve being slidable on that smaller diameter member.

To allow for use of the device with syringe-needle units of different sizes, the device can be provided in different form wherein the bores correspond to such as is required for holding the syringe barrel relatively snugly. Also, an adapter piece can be received on the other end of the holder body to increase the length thereof in correspondence to the use of the device with a syringe-needle unit wherein the needle tip end of such unit would otherwise project beyond the said one end of the sleeve when said sleeve was extended.

The invention accordingly comprises the features of construction, combination of elements, and arrangement of parts of the device which will be exemplified in the construction hereinafter set forth and the scope of the invention will be indicated in the claims.

BRIEF DESCRIPTION OF THE DRAWINGS

A fuller understanding of the nature and objects of the invention will be had from the following detailed description taken in conjunction with the accompanying drawings, in which:

FIGS. 1a, 1b and 1c are perspective views on reduced scale depicting the manner in which the device of the present invention is employed for receiving and holding a hypodermic syringe-needle unit incident to administration therewith of a medicament such as insulin to a user;

FIG. 2 is a longitudinal central sectional view of a first form of the device of the invention wherein magnetic sleeve detent means are employed, and wherein the sleeve is shown in extended position and the hypodermic syringe-needle unit in full lines;

FIG. 3 is a side elevational view on enlarged scale, partly in section showing the manner of placement of the device with the sleeve thereof extended against the body part preliminary to effecting needle insertion into the body part;

FIGS. 4 and 5 show on enlarged scale respective second and third embodiments of the device wherein the sleeve detent means includes a laterally widened shoulder on the holder and a resiliently yieldable end structure on the sleeve, the sleeve in the FIG. 4 embodiment being in extended position but that of the FIG. 5 embodiment retracted; and FIG. 6 is a perspective view of the resiliently structured sleeve used with the FIGS. 4 and 5 embodiments.

Throughout the following description, like reference numerals are used to denote like parts in the drawings.

DESCRIPTION OF THE PREFERRED EMBODIMENTS

The further description of the invention given herein will be set out with particularized reference to use of the device by diabetics for self-administering of insulin to themselves. It will be appreciated however that the device can be used for a wider range of hypodermic syringe administered injections inclusive of use in hospitals, laboratories and the like. Also and in appropriate circumstances it could be used where hypodermic syringes are used for withdrawing or aspirating body fluids for test purposes and the like.

With reference first to FIGS. 1a–1c, which show the sequence of steps involved in using the device, the device 20 (illustratively, the FIG. 2 embodiment) includes a preferably cylindrical holder 22 having a section 24 of larger diameter and a section 25 of smaller diameter. Captively slidable on section 25 is a sleeve 26, the sleeve being slidable between the retracted position shown in FIGS. 1a and 1b and the extended position shown in FIG. 1c. The holder has a through bore 28. The hypodermic syringe-needle unit 30 is of conventional construction and includes a barrel 32 at the tip end of which is fitted a needle 34, the needle in FIG. 1a being covered over by a protective cap 36 received on the barrel. The present invention is intended primarily for use with so-called "disposable" type syringe units but it nonetheless contemplates use with reusable type syringes as well. At the rear end of the barrel is the customary finger flange 38 and a piston rod 40 is shown extended outwardly from the barrel and terminating in a head cap 42 thus indicating that the syringe-needle unit has been preloaded with the requisite quantity of insulin the diabetic is to self-administer. As a first step the user aligns the hypodermic syringe-needle unit with the bore 28 of the device of the invention and then inserts same into the device, the bore desirably being such as to provide a friction held fit of the barrel with the bore. The degree of fit generally precludes other than deliberate applied removal force exerted upon the syringe-needle unit from causing the two to separate in normal usage. Alternatively as will appear later, the holder can be fitted with a set screw for engaging the syringe-needle unit barrel to hold it securely in place. Most conveniently though the bore/barrel fit will involve close manufacturing tolerances to give a good, secure yet easily insertable-removable barrel fit. The device will of course be made with varying size bores to match the various barrel size syringes available. With the hypodermic syringe-needle unit received in the bore 28 and as shown in FIG. 1b, the needle 34 will project beyond the end of the holder 20 since the sleeve 26 is in retracted position. The user then removes the protective cap 38 and as shown in FIG. 1c, slides the sleeve to its extended position so that the sleeve thereby encircles the needle and extends beyond the tip end thereof. The device can then be placed contactingly against the surface of the body part 44, e.g., an arm or a thigh at which the injection is to be made. Thereafter by unitarily sliding the holder 22 and the hypodermic syringe-needle unit 30 toward the body part (rightwardly in FIG. 3), the detent force holding the sleeve 25 in extended position will be overcome by such unitary sliding movement and the needle will be caused to penetrate the body part with the sliding unitary movement being terminated when the larger diameter holder section 24 comes into abutment with the sleeve unit 25 and at which point the needle will have penetrated the body to the depth L which measure of penetration will be the same each and every time the unit is employed. The user then will move the plunger 40 rightwardly (FIG. 3) to pump or otherwise dispense the insulin contents from the barrel into his body.

Referring more specifically now to the first embodiment 20 of the device shown in FIG. 2 in greater detail, it includes the holder 22 which is comprised of a first cylindrical larger diameter elongated component or section 24 having a bore 28a passing therethrough, and a second elongated lesser diameter holder section 25 which has a companion dimensioned aligned bore 28b matching that of the section 24. The larger section 24 is axially bored as at 50 for receiving in friction fit therewith, the section 25, the degree of friction fit being such as to prevent ready separation of these two components except with a deliberate force action intended to produce such result. The right end of the holder which is defined by the enlarged boss 52 at the rightward end of section 25 is located such that when the barrel 32 of the syringe-needle unit 30 has been received in the aligned bores 28a and 28b, the needle 34 will extend rightwardly some distance beyond the boss end of the holder and the finger piece 38 of the syringe-needle unit will be in nesting abutment with the left end of the holder, the holder including at that left end and received in an axial bore 56 formed therein, an adapter piece 58 the use of which will be explained shortly. Slidably, captively received on section 25 of the holder is the elongated sleeve 26 being depicted in FIG. 2 in its extended or rightmost position in which it encircles the needle 34 of the syringe-needle unit and the sleeve right end projecting some distance beyond the tip end of the needle. The retracted position of the sleeve is shown in dashed lines and from which depiction it will be noted that with the sleeve in the retracted position the needle tip end will extend nakedly beyond the device. Preliminary to inserting the syringe-needle 30 unit into the holder 22, the user will have first filled the syringe with the requisite quantity of insulin that he is to self-administer and for which purpose the piston 60 which is connected to the rod 40 will be positioned correspondingly at the requisite associated volume graduations 63 found on the barrel of the syringe. The user will then (refer to FIG. 1b) remove the protective cap 36 from the covering position over the needle 34 and slide the sleeve 26 rightwardly from retraction to extended positions. In the extended position, the sleeve which carries at the rear end thereof as by press fit, adhesive securement or the like, a magnet 70 of annular encircling compass about section 25, will become held in detented position by reason of the presence of a second like configured magnet or ferromagnetic material component 72 disposed securely on section 25 adjacent the boss 52 at the right end of that holder section. The magnetic force attraction between the two magnetic components 70 and 72 is sufficient to prevent initiation of any retraction movement of the sleeve as when the user proceeds to contactingly place the right end of the sleeve against the body part in which the injection is to be made and as can be seen in FIG. 3. The release of the detent means can only readily be effected by the user applying rightward unitary sliding producing force to the syringe unit 30 and the holder 22 and in so doing, the amount of force required to release the detent and effect relative retraction of the sleeve will be of only marginally higher magnitude than detent holding but it will result in the enactment of a controlled sliding travel of the needle that will allow easy uniform needle stroking and minimized discomfort producing penetration of the user's body. When the right end of holder section 24 comes into abutment with the left end 73 of sleeve 26, the sliding unitary travel of the syringe and the holder will be terminated and the maximum penetration depth of the needle arrived at. The user thereafter by pressing the plunger 40 rightwardly will expel the contents of insulin from the syringe into his body.

Referring to FIG. 4, the embodiment 80 of device shown therein differs from that previously described in that the holder 82 in which the syringe is received is made as a single piece cylindrical component having a section 84 of larger diameter and an axially aligned section 86 of smaller diameter, the smaller diameter section enlarging towards the right end thereof as at 88 to provide detent and sleeve capture structure thereon as will be described in detail shortly. The details of the hypodermic syringe-needle unit 30 are in all respects the same as those previously given. The device 80 differs principally from that previously described in that the detent means provided complementally on the holder 82 and sleeve 90 are provided by specific detenting structure formed on those two components. Thus the section 86 of reduced diameter near the right end thereof has a slight incline surface 92 which leads to a rightwardly adjacently disposed laterally widened encircling shoulder 94 on the section 86, and immediately adjacent rightwardly situate thereto is a shoulder stop abutment formation 96 which precludes ultimate sliding removal of the sleeve entirely from the holder body. The sleeve 90 as seen in FIG. 6 at the left end thereof is resiliently structured at such end, having a plurality of circularly spaced ribs 100 formed therein, the respective ribs being separated by longitudinal blind slots 102 formed in the sleeve and the tip ends of the ribs including radially inturned portions 104. Thus when the sleeve 90 is slid from the dashed line retracted position shown in FIG. 4 to the extended rightward full line position thereof, the inturned projections 104 on the respective ribs ride up the inclined surface 92 of section 86 and seat upon shoulder 94. In so doing, the ribs elastically yield radially outwardly to be accommodated on such shoulder surface and in assuming such resiliently biased condition, they apply a biasing force counter to the direction of radial yield movement to thereby tightly engage the shoulder 94 to hold the sleeve detented in the extended position. Thus and in fashion comparable to the releasing force required to separate the magnets in the previously described embodiment, a certain magnitude of force is required to initiate the relative leftwardly retractive movement of the sleeve during the time the insertion of the needle into the user's body is being effected. In the FIG. 4 embodiment, means also are provided if necessary to securely fix the syringe barrel 32 within the bore 28a, 28b of the holder. As was previously indicated, this accommodation could be one of friction fit but where such fitment is not sufficient to insure proper retention of the barrel within the holder, set screw 110 can be received in a side bore opening 112 of the holder body and can be used to apply set screw pressure to the syringe barrel for securement thereof and particularly as an incident to the effecting of unitary sliding movement of the syringe unit and holder body during the insertion step.

The embodiment 120 shown in FIG. 5 is generally of the same construction as that relating to the FIG. 4 embodiment except the holder body is made in separable alignable sections 122 and 124 and an adapter piece 126 is used at the left end of the holder body for the same reasons as given earlier in connection with embodiment 20. The sleeve 90 of the FIG. 5 construction is shown in the retracted position and when the sleeve is slid rightwardly to its extended position, the inturned portions 104 of the sleeve which is slotted in the fashion depicted in FIG. 6, ride upwardly on incline 92 and engage with shoulder 94 on a body section 124, the radially outwardly yielding of the rib sections of the sleeves being shown in dashed lines in this figure.

From the foregoing description it is believed that those skilled in the art will readily appreciate the advantages provided by the present invention for use in administering injections with hypodermic syringe-needle units and particularly so where self-administering is being carried out by the diabetic. While there are disclosed only certain embodiments of the device it will be further appreciated that various modifications can be made therein by those skilled in the art yet remain within the scope of the inventive concept disclosed.

What is claimed is:

1. Device for facilitating insertion of the needle of a hypodermic syringe-needle unit into a human body part during employment of such unit for injection or fluid aspiration purposes, said device comprising:

an elongated holder for reception and encirclement of the syringe-needle unit with the needle extending a distance beyond one end of the holder, a sleeve captively received on said holder and slidable thereon from a retracted position wherein one end of said sleeve is proximate said one end of the holder to an extended position wherein the sleeve encircles the needle and its said one end projects beyond the needle tip end, and cooperating detent means carried on said sleeve and said holder and operable when said sleeve is in extended position for inhibiting initiation of retraction sliding of said sleeve when said one end of said sleeve is contactingly placed by the user against the body part for positioning the needle tip end proximate said body part, said detent means comprising magnet means carried on the said one end of said holder and the other end of said sleeve, said detent means being readily releasable under the impetus of the force resulting from the user effecting unitary needle insertion movement of said holder and syringe-needle in the direction of the body part, said unitary movement being terminated by abutment engagement of said holder against said sleeve and correspondingly the depth of penetration of the needle into the body limited.

2. The device of claim 1 in which said holder has a central bore extending end to end thereof in which the barrel part of the hypodermic syringe is received, the holder having coaxially aligned sections of greater and lesser thickness, the needle of said unit extending beyond the holder section of lesser thickness and the sleeve being slidable on said lesser thickness section and when in retracted position its other end abutting against the holder section of larger thickness.

3. The device of claim 2 in which the holder is a single piece component formed with integral longitudinal sections of greater and lesser thickness.

4. The device of claim 2 in which the holder is comprises of separate elongate members of respective greater and lesser thicknesses, each member having longitudinal through bores of the same dimension, the member of greater thickness having an axially directed socket for reception of the other member with the bores thereof aligned.

5. The device of claim 4 in which the holder member of lesser thickness is removably received in the larger thickness member socket.

6. The device of claim 5 in which the holder member of lesser thickness is received in the larger thickness member socket with a friction fit thereto.

7. The device of claim 1 further comprising locking means carried in said holder and engagable with a syringe-needle unit received therein to prevent relatively sliding movement therebetween.

8. The device of claim 1 in which the holder is provided with a through bore in which the syringe-needle unit is received, the bore being sized such as to receive the syringe barrel in friction fit therewith.

9. The device of claim 1 further comprising an adapter piece mountable on the other end of said holder to increase the length thereof in correspondence to the use of the device with a syringe-needle unit wherein the needle tip end of such unit has a length which would otherwise project beyond the said one end of the sleeve when said sleeve was extended.

10. A method for injecting medication from a hypodermic syringe-needle unit into the human body comprising supporting the syringe-needle unit in the device of claim 1 and while so supported effecting the desired injection.

11. Device for facilitating insertion of the needle of a hypodermic syringe-needle unit into a human body part during employment of such unit for injection or fluid aspiration purposes, said device comprising:

an elongated holder of elongated coaxially aligned commonly externally configured sections one of which is narrower than the other, the sections having communicating through bores of the same dimension, the syringe-needle unit having a barrel received in close-fitting frictionally retained reception in said communicating bores and such that the needle extends a distance beyond the end of the narrower holder section, a sleeve captively slidable in the narrower holder section from a retracted position wherein one end of said sleeve is proximate the said end of the narrower holder section and the other sleeve end abuts the said other holder section to an extended position where the sleeve encircles the needle and its said one end projects axially a distance beyond the needle tip end, and cooperating detent means carried on said sleeve and said holder and operable when said is in extended position for inhibiting initiation of retraction sliding of said sleeve when said one end of said sleeve is contactingly placed by the user against the body part for positioning the needle tip end proximate said body part, the said narrower holder section including a boss on the said end thereof, the sleeve sliding on said boss, the detent means comprising a magnet member fixed on said narrower holder section adjacent said boss and another magnet fixed within said sleeve at the said other end thereof, said detent means being readily releasable under the impetus of the force resulting from the user effecting unitary needle insertion movement of said holder and syringe-needle in the direction of the body part, said unitary movement effecting relative retraction of said sleeve, said movement being terminated by abutment engagement of the said other holder section with the said other sleeve end and correspondingly the depth of penetration of the needle with the body limited.

12. The device of claim 11 in which the first-mentioned magnet encircles the narrower holder section and the said other magnet follows a like encircling course.

* * * * *